US011008243B2

(12) United States Patent
Baumann et al.

(10) Patent No.: US 11,008,243 B2
(45) Date of Patent: May 18, 2021

(54) METHOD FOR PRODUCING A SYRINGE HAVING A PIERCING MEANS

(71) Applicants: Gerresheimer Regensburg GmbH, Regensburg (DE); Gerresheimer Bünde GmbH, Bünde (DE)

(72) Inventors: Manfred Baumann, Schirmitz (DE); Michael Wiglenda, Irchenrieth (DE); Claudia Petersen, Hannover (DE)

(73) Assignees: Gerresheimer Regensburg GmbH, Regensburg (DE); Gerresheimer Bunde GmbH, Bunde (DE)

( * ) Notice: Subject to any disclaimer, the term of this patent is extended or adjusted under 35 U.S.C. 154(b) by 161 days.

(21) Appl. No.: 16/036,943

(22) Filed: Jul. 17, 2018

(65) Prior Publication Data
US 2019/0023602 A1 Jan. 24, 2019

(30) Foreign Application Priority Data

Jul. 18, 2017 (EP) .................................. 17181771

(51) Int. Cl.
*C03B 23/049* (2006.01)
*A61M 5/28* (2006.01)
(Continued)

(52) U.S. Cl.
CPC .......... *C03B 23/0496* (2013.01); *A61M 5/28* (2013.01); *A61M 5/3129* (2013.01);
(Continued)

(58) Field of Classification Search
None
See application file for complete search history.

(56) References Cited

U.S. PATENT DOCUMENTS

2003/0220613 A1* 11/2003 Fabian .................. A61M 5/343
604/187
2004/0065116 A1* 4/2004 Vetter ................ B23K 26/0734
65/29.19
(Continued)

FOREIGN PATENT DOCUMENTS

CN 102470221 5/2012
CN 103906540 7/2014
(Continued)

OTHER PUBLICATIONS

European Search Report, dated Feb. 5, 2018, corresponding to European Application No. 17181771 (filed Jul. 18, 2017), parent of the present application, 3 pages.
(Continued)

*Primary Examiner* — Lisa L Herring
(74) *Attorney, Agent, or Firm* — Leydig, Voit & Mayer, Ltd.

(57) ABSTRACT

The invention relates to a method for producing a syringe having a piercing means, comprising the following steps: a) providing a syringe body having a distal end section, which comprises an inner channel that discharges at a distal opening, wherein the distal end section is in a formable state; b) providing a piercing means; c) inserting a proximal section of the piercing means through the distal opening into the inner channel of the distal end section; and d) shaping the distal end section by means of a first shaping tool in such a way that an inner surface of the distal end section contacts at least portions of the piercing means, as a result of which at least portions of the piercing means are secured.

20 Claims, 8 Drawing Sheets

(51) Int. Cl.
*A61M 5/31* (2006.01)
*A61M 5/34* (2006.01)
*C03B 23/26* (2006.01)

(52) U.S. Cl.
CPC ............ *A61M 5/343* (2013.01); *A61M 5/349* (2013.01); *C03B 23/26* (2013.01); *A61M 2207/00* (2013.01); *A61M 2207/10* (2013.01)

(56) References Cited

U.S. PATENT DOCUMENTS

| | | | |
|---|---|---|---|
| 2013/0231617 A1* | 9/2013 | Hoppe | A61M 5/343 604/272 |
| 2015/0114043 A1* | 4/2015 | Risch | C03B 23/043 65/29.18 |
| 2015/0374931 A1* | 12/2015 | Sugiki | A61M 5/343 604/240 |

FOREIGN PATENT DOCUMENTS

| | | |
|---|---|---|
| CN | 104159857 | 11/2014 |
| CN | 105188814 | 12/2015 |
| CN | 105530979 | 4/2016 |
| CN | 106565076 | 4/2017 |
| DE | 10 2012 101948 | 9/2013 |
| DE | 10 2015 117212 | 4/2017 |
| EP | 1364670 | 5/2003 |
| EP | 3431123 | 1/2019 |
| WO | WO 2008/139982 | 11/2008 |
| WO | 2017/060052 | 4/2017 |

OTHER PUBLICATIONS

China National Intellectual Property Administration, "1st Office Action," dated May 25, 2020, corresponding to Chinese Patent Application No. 201810723141.4, 12 pp.

China National Intellectual Property Administration, "2nd Office Action," dated Jan. 6, 2021, corresponding to Chinese Patent Application No. 201810723141.4, 19 pp.

* cited by examiner

METHOD FOR PRODUCING A SYRINGE HAVING A PIERCING MEANS

CROSS-REFERENCE TO RELATED APPLICATIONS

This application claims priority from European Patent Application No. EP 17 181 771.1, filed Jul. 18, 2017, which is incorporated by reference herein in its entirety.

BACKGROUND OF THE INVENTION

The invention relates to a method for producing a syringe having a piercing means.

The term syringe is understood to mean a medical receptacle, the distal end of which is equipped with a piercing means. It is also conceivable that the method will be applicable to additional medical receptacles made of glass. The term piercing means should be understood to mean a cannula, a needle, or the like. Furthermore, the invention is mainly related to glass syringes, with application in the area of plastic syringes being entirely conceivable.

Syringes of this kind comprise a hollow, cylindrical syringe body where the medium being administered is located, a distal end of which terminates in a hollow, cylindrical end section. The inner diameter of the end section in this case is smaller than the inner diameter of the syringe body. Furthermore, the outer diameter of the syringe body is larger than the outer diameter of the end section. This end section is normally conical in shape. Accordingly, an end section of this kind is frequently referred to as a nozzle or a syringe cone. At the proximal end of the syringe body, there is an insertable plunger, which has a stopper and can be used to administer the medium.

The terms "distal" and "proximal" are to be understood such that the distal end of the syringe is closer to the administration site, and the proximal end is farther away from the administration site. The terms "distal and proximal direction" are to be understood in a similar manner.

The production of prefillable glass syringes normally takes place by forming sections of glass tubes which serve as a preform, followed by reshaping at high temperatures. The reshaping process uses shaping tools exhibiting sufficient heat deflection temperature properties and wear resistance properties along with high ductility. The glass syringes are normally produced using highly chemical-resistant and heat-resistant types of glass such as borosilicate glass or quartz glass. The syringe cone in this case comprises a channel connecting the cannula and the syringe chamber, where the medium being administered is retained.

In this context, the syringe cone is produced by heating the glass tube section-by-section. If the glass is in a formable state, then the external shape is produced by means of a second shaping tool, and the internal shape by means of a so-called shaping pin or shaping mandrel, which is a component of a first shaping tool.

In addition to other designs, the syringe cone can be designed as a so-called Luer cone, which is able to accept a corresponding piercing means. Prefillable and deliverable syringes are often furnished with so-called "staked-in needles (SIN)". In this case, the cannula is typically secured in the channel by means of an adhesive connection. In order to facilitate adhesion of the cannula, it is normally necessary for the channel in SIN syringes to have a smaller diameter than syringes with a Luer cone.

In this case, the cannula is initially introduced into the distal end of the syringe before being secured in the end section by an adhesive. Typically, an organic adhesive is used which can be cured using UV light. Having been furnished with the cannula, the syringe is then sterilised and filled with the appropriate medium. Filling can take place immediately thereafter or at an appropriate pharmaceutical company. After filling, the stopper is inserted at the proximal end of the syringe body.

In the prior art, the adhesive connection between the cannula and an inner surface of the end section exists along the entire length of the end section of the syringe body. After the medium has been filled, it is then in direct contact with the adhesive. As a result, the components of the adhesive can diffuse into the medium or medication or rather interact with it. This effect can be further intensified due to insufficient curing of the adhesive residue. These impurities can have a highly negative impact on modern active ingredients. In order for their optimal effects to be guaranteed, complex and sensitive medicines of this kind need to be protected more strongly than ever from possible contaminants.

The DE10 2010 045 095 B4 document presents a solution for this problem which entirely omits an adhesive. The glass at the interior of the cone opening is heated once again by means of radiation, thus achieving a material connection between the glass body and the cannula. This has the disadvantage of requiring the use of an appropriately modified glass, which is accordingly able to absorb electromagnetic radiation.

In the EP1370314B1 document, the problem is solved by means of a stop, which is located in the cone opening and seals the cannula. After introduction, the cone opening is filled with adhesive in order to ensure the necessary pullout forces for the cannula. The disadvantage of this approach is the precise and therefore cost-intensive shaping of the inner stop within the cone opening. As a result, the precision with which this stop is manufactured is decisive in whether the adhesive is able to reach the interior of the syringe cylinder.

Therefore, an object of the invention is to provide a method for producing a syringe having a piercing means, said method ensuring that the piercing means is secured in the end section in a simple manner while also preventing contamination within the syringe body. It is furthermore an object of the invention to provide a corresponding syringe.

SUMMARY OF THE INVENTION

The above problems are solved by means of a method for producing a syringe having a piercing means, comprising the following steps:
  a) providing a syringe body having a distal end section, which comprises an inner channel that discharges at a distal opening, whereby the distal end section is in a formable state;
  b) providing a piercing means;
  c) inserting a proximal section of the piercing means through the distal opening into the inner channel of the distal end section;
  d) shaping the distal end section by means of a first shaping tool in such a way that an inner surface of the distal end section contacts at least portions of the piercing means, as a result of which at least portions of the piercing means are secured.

By means of the invention, a method is now being provided which provides an exceptionally simple way of securing the piercing means. No particular modifications have to be taken into account when producing the syringe body. In particular, the distal end section can preferably be produced to have a simple channel without a stop for the piercing means. Having been inserted into the channel through the distal opening, the piercing means is then secured by means of said contact with the inner surface of the shaped section. The term "securing the piercing means" is understood to mean attaching the piercing means so that a pullout force, meaning the force that must be exerted in order to pull the piercing means out of the channel, of at least 30N, preferably at least 60N, and more preferably at least 90N, can be withstood.

The syringe body preferably consists of borosilicate glass or quartz glass. However, applying the method to a syringe body consisting of plastic would also be conceivable.

Preferably, the formable state of the distal end section is generated by means of heating. A large variety of means can be used for this purpose, for example burners, radiation sources, or lasers. When using the method for a glass syringe, the temperature of the distal end section would fall within a range between 1000° C. and 1200° C., preferably 1100° C.

According to an embodiment of the present invention, producing the syringe body comprises the following steps:
  aa) providing a hollow, cylindrical glass preform, which extends along direction (X) and has at least one open distal end, whereby the glass preform features a shaped section that extends from the open distal end in an axial direction (X) and is in a formable state;
  bb) shaping the shaped section to the preferably cone-shaped distal end section of the syringe body by means of a second and a third shaping tool.

Said production steps aa) and bb), hence the shaping of the shaped section to the distal end section, are performed prior to step a), which is providing a syringe body having a distal end section.

According to an embodiment of the invention, step bb) comprises the following sub-steps:
  (1) providing the second shaping tool, by means of which at least the shaped section of the hollow, cylindrical glass preform is able to be shaped;
  (2) providing a third shaping tool, which features a shaping pin;
  (3) inserting the shaping pin through the open distal end of the hollow, cylindrical glass preform and into the shaped section thereof;
  (4) shaping the shaped section by means of the second shaping tool such that the inner surface of the shaped section fits against the shaping pin, as a result of which the shaped section forms the channel;
  (5) removing the shaping pin from the channel.

The shaping of the distal end section in step d) preferably takes place immediately after the syringe body is produced. The distal end section would therefore still be in a formable state after the insertion of the piercing means, thus enabling the further shaping in step d) to be performed.

However, the syringe body can initially also be subjected to an additional process, in which the distal end section is heated so that it is again transformed into a formable state. This process can include the aforementioned means such as burners, radiation sources, or lasers.

According to an embodiment, and in steps b) and c) in particular, the piercing means is rotatably mounted in a holding device. The piercing means preferably consists of a stainless steel. Conventional cannulae have particular, very fine cuts, such as a single cut, a facet cut, or a V-bevel-cut. In this context, it is advantageous for the cut to assume a certain position in relation to the syringe body, for example during the further processes such as putting a protective cap in place. The orientation of the cut in relation to a finger flange is also advantageous for the use of the syringe. Accordingly, a sensing means can advantageously detect the orientation of the piercing means or rather the cut in relation to the piercing means within the holding means. The cannula can then be properly oriented by means of rotatable mounting.

According to a further embodiment, the distal end section has a length (L). Preferably, the shaping in step d) takes place along at least a sub-section of the length L. A contact section of the channel or rather the inner surface of the distal end section preferably contacts the piercing means thereby. As a result, the piercing means is preferably secured in at least a rudimentary manner. Preferably, the entire circumference (U) of the piercing means is completely contacted by the inner surface of the distal end section.

Preferably, the length (L) of the distal end section extends between a main section of the syringe body, in which the medium can be kept—or rather a transitional area between the main section and the distal end section—and the distal opening, through which the piercing means was inserted. The contact section of the channel is preferably located at the end of the length (L) leading to the main section of the syringe body. The result of the entire circumference (U) of the piercing means fitting against and along the inner surface of the end section is not only securing the piercing means; penetration of contamination into the main section of the syringe body is also prevented. It is advantageous for the contact section to extend along 5% to 90% of the length (L) of the distal end section, preferably along 20% to 80% of the length (L) of the distal end section, and particularly preferably along 30% to 50% of the length (L) of the distal end section.

According to an embodiment, following the shaping in step d), a preferably organic adhesive is introduced through the distal opening into a distal section of the channel, thereby further securing the piercing means to the distal end section. The term "securing the piercing means" is understood to mean attaching the piercing means so that a pullout force, meaning the force that must be exerted in order to pull the piercing means out of the channel, of at least 30N, preferably at least 60N, and more preferably at least 90N, can be withstood. The use of a polymer-based or epoxy-based adhesive is preferable.

The adhesive is preferably introduced through the distal opening. By means of the preferable use of an initiator, the activation thereof can result in the adhesive already being pre-cured. Final curing can then preferably take place during a curing process. The means suitable for this purpose depend on the adhesive being used. Preferably, UV curing or thermal curing may take place.

The result of the entire circumference (U) of the piercing means fitting against and along the inner surface of the end section is not only securing the piercing means; unwanted penetration of adhesive into the main section of the syringe body is also prevented.

According to an embodiment, the shaping in step d) takes place across essentially the entire length (L) of the distal end section. A contact section of the channel or rather the inner surface of the distal end section preferably contacts the piercing means thereby. As a result of this contact, the piercing means is preferably secured such that a pullout force of at least 30N is achieved without the use of an additional adhesive. Preferably, the entire circumference (U) of the piercing means is completely contacted by the inner surface of the shaped section.

Preferably, the length (L) of the distal end section extends between a main section of the syringe body, in which the medium can be kept—or rather a transitional area between the main section and the distal end section—and the distal opening, through which the piercing means was inserted. The contact section of the channel is preferably located at the end of the length (L) leading to the main section of the syringe body and extends across essentially the entire length (L). As a result of the entire circumference (U) of the piercing means fitting against and along the inner surface of the end section and the contact section extending across essentially the entire length (L), the piercing means is effectively secured. As a consequence, the use of an adhesive can be entirely omitted. The entire circumference (U) of the piercing means fitting against and along the inner surface of the shaped section furthermore prevents penetration of contamination into the main section of the syringe body.

According to an embodiment, the first and/or the second shaping tools comprise two shaping rollers which are spaced apart from one another. In a first position, the shaping rollers are preferably spaced apart by a first distance, whereby the distal end section of the syringe body, or rather the hollow cylindrical glass preform, is displaceable between the shaping rollers when the shaping rollers are located in the first position.

The shaping rollers of the second shaping tool are preferably displaceable into a second position, in which they are spaced apart by a second distance, which is smaller than the first distance. In the second position, a deforming force is preferably able to be applied to the shaped section of the hollow, cylindrical glass preform by means of the shaping rollers, as a result of which the external shaping of the shaped section can be accomplished. Advantageously, an internal shaping of the shaped section can in this case be accomplished by means of the third shaping tool.

The width of the shaping rollers of the first shaping tool is preferably smaller than or equal to the length (L) of the distal end section. By means of the shaping rollers having a width which essentially conforms with the length (L) of the distal end section, a contact section can be formed which essentially conforms with said length (L). By means of the shaping rollers having a width smaller than the length (L) of the distal end section, a correspondingly smaller contact section can be shaped.

The shaping rollers of the first shaping tool are preferably displaceable into a second position, in which they are spaced apart by a distance which is smaller than the first distance. In the second position, a deforming force is preferably able to be applied to the distal end section by means of the shaping rollers, as a result of which the shaping of the distal end section is able to be accomplished, and the inner surface of the distal end section is pressed against the piercing means.

According to an embodiment, the initial shaping of the distal end section in step bb) and the further shaping of the distal end section in step d) takes place by means of the first shaping tool. Accordingly, following the shaping of the shaped section to the distal end section, the shaping pin is removed from the channel and the third shaping tool is removed. The holding device along with the piercing means is subsequently arranged so as to enable the piercing means to be inserted centrically in relation to the axial centre line of the syringe body. Further shaping can take place by means of the same shaping rollers of the first shaping tool. It would be conceivable to structure the shaping rollers so that their width is able to be varied. The contact section can then be designed accordingly.

When using two shaping tools (the first and the second shaping tool), the shaping pin of the glass preform is removed from the gap between the shaping rollers of the second shaping tool and then placed into the gap in the first shaping tool. The advantage in doing so is that the holding device for the piercing means and the third shaping tool are aligned with the shaping pin of the shaping rollers of the first or rather the second shaping tool.

Preferably, the hollow, cylindrical glass preform is arranged in a holding device such that said preform is rotatable, whereby the axis of rotation is the axial centre line of the hollow, cylindrical glass preform. The third shaping tool, which has the shaping pin, is preferably arranged centrically with respect to said axial centre line.

When the inner surface is being pressed against the piercing means, the shaping rollers of the first shaping tool preferably remain in a fixed position. In order to then achieve contact for the piercing means around the entire circumference (U) of the piercing means, the syringe body can advantageously be rotated by means of the holding device. During this process, the piercing means can preferably be rotated by means of the rotatable holding device in a manner appropriately synchronous with the holding device for the syringe body.

As an advantageous alternative, after having initially been secured in places, the piercing means can be released from its holder enough to allow rotation of the syringe body. Due to having initially been secured in places, a sufficiently strong frictional connection already exists in order to ensure doing so. As a result, the holder preferably then functions only as a guide for rotating the piercing means.

Whereas the shaping tools on the exterior of the tube are uncritical since any potential abraded material will not come into contact with the filled contents, all of the tools being used within the glass preform can be considered to be critical. The tools currently being used in the prior art consist of nearly 100% tungsten. This material is quite well-suited for tools that lie against the exterior, but it is less well-suited for tools used within the glass receptacle. The shaping pin for the channel in the syringe cone is very small and, due to its limited thermal capacity, heats up intensely, thus leading to the occurrence of oxides which cause wear and abrasion. The magnitude of abrasion of the shaping pin is such that the shaping pin normally needs to be replaced after approximately 1 hour of operation. This abraded material precipitates into the channel, where it is later absorbed by the filled contents, thus leading to a degradation of efficacy and compatibility.

Accordingly, the shaping pin preferably consists of a non-metallic material, for example a technical ceramic, a ceramic-like material, or glass-like carbon. Ceramic materials are polycrystalline, inorganic, and non-metallic. They are normally formed at room temperature from a mass of raw material and obtain their typical material properties by means of a sintering process which takes place at high temperatures. The term "technical ceramic" is the generic term for ceramic materials and the products made from them and used for technical applications. Technical ceramics are furthermore divided into silicate ceramics, oxide ceramics, and non-oxide ceramics. The non-oxide ceramics are furthermore differentiated into carbide and nitride non-oxide ceramics.

It is particularly preferable for the shaping pin to consist of silicon nitride ($Si_3N_4$) or glass-like carbon. Additional preferable materials are zirconium oxide and zirconium toughened alumina oxide (ZTA). Silicon nitride is a non-oxide ceramic and exhibits high fracture toughness and low thermal expansion coefficients. It has a continuous use temperature of 1300° C. and a relatively high ability to withstand temperature fluctuations. Glass-like carbon or glassy carbon has a particularly low tendency to adhere to the glass preform during the shaping process but has a continuous use temperature of only 600° C. However, its continuous use temperature can be increased to over 2000° C. given the use of a protective gas atmosphere.

According to an embodiment, the shaping pin is cooled by a cooling means, thus increasing the service life of the shaping pin.

Following step d), having been provided with the piercing means, the syringe body is advantageously cooled and/or subjected to a sterilisation process. This sterilisation process can take place by means of liquids or vapours. A dry sterilisation process by means of heating would also be conceivable. Furthermore, a lubricant such as silicone oil can be applied to the inner surface of the main section. The syringes can then be provided with needle protection and packaged in trays or cartons. The syringes are then normally filled by a pharmaceutical manufacturer. The plunger, which has a stopper, is inserted thereafter.

The problem is furthermore solved by means of a syringe having a piercing means which is produced by means of a method according to any of the preceding claims.

Additional advantages, objectives, and characteristics of the present invention will be explained in reference to the attached drawings. Among the various embodiments, similar components may have the same reference signs.

DETAILED DESCRIPTION OF THE INVENTION

Figure 1:
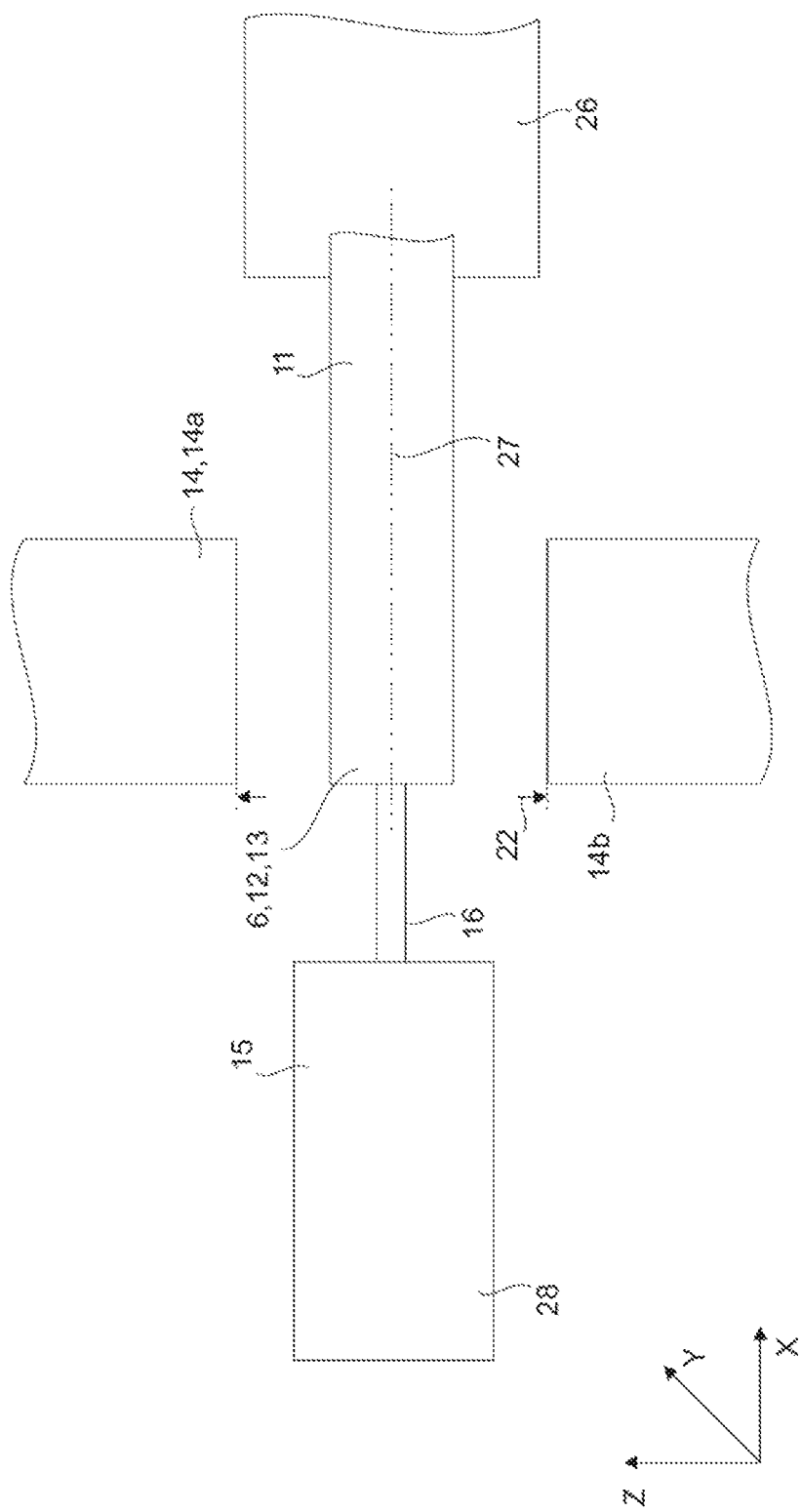
FIG. 1 is a schematic depiction of a method for producing a syringe body in an embodiment of the invention.
Figure 2:
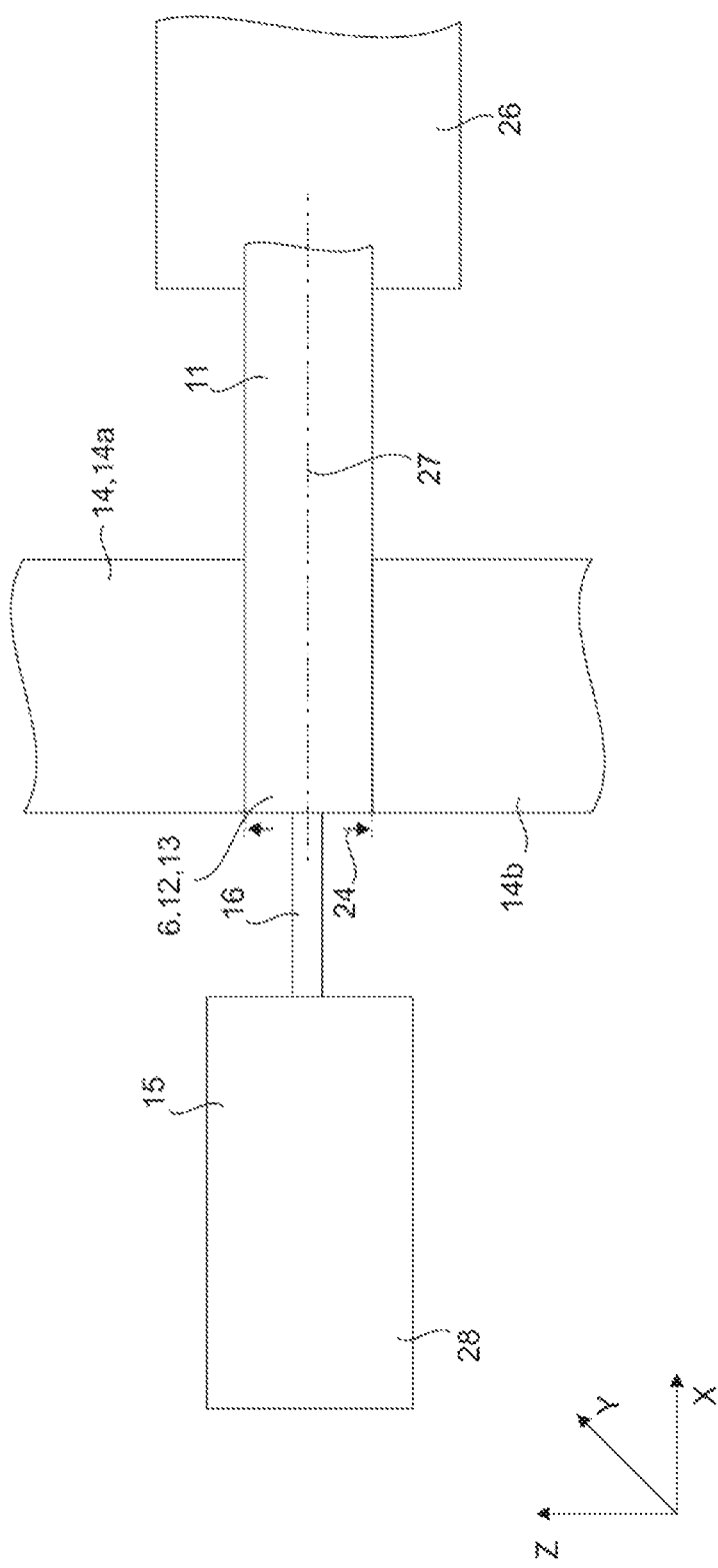
FIG. 2 a further schematic depiction of the method for producing a syringe body.
Figure 3:
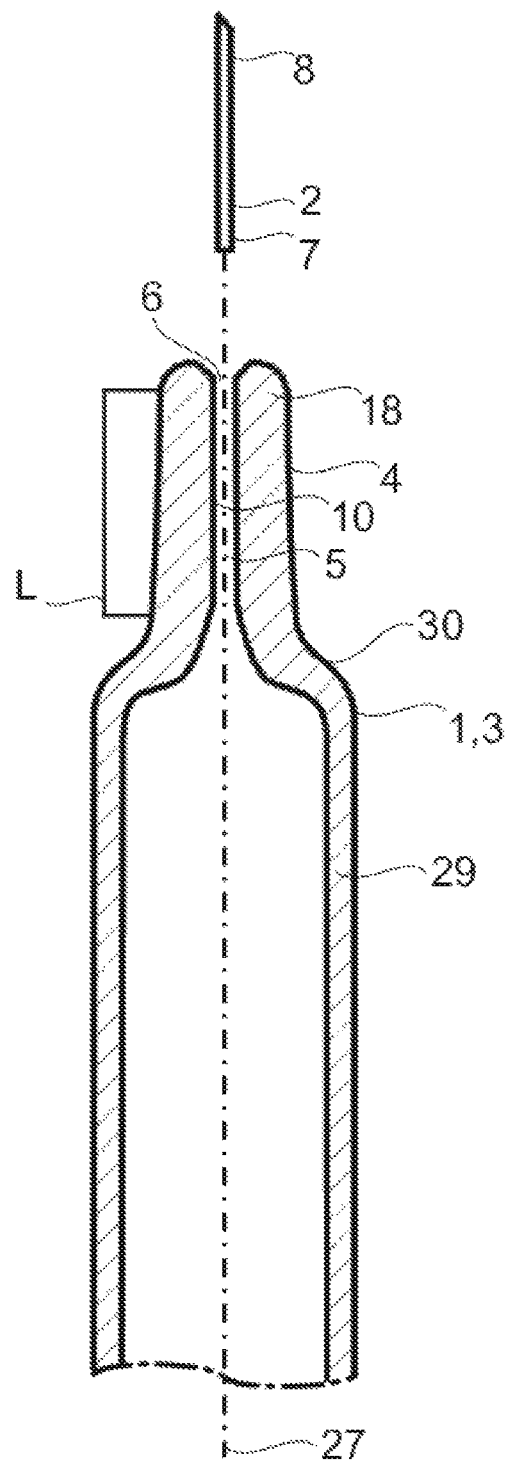
FIG. 3 shows a sectional view of a syringe body and a piercing means.

FIGS. 1 and 2 show a schematic depiction of a method for producing a syringe body (3) having a distal end section (4). A syringe body (3) of this kind is illustrated in FIG. 3 and is produced from a hollow, cylindrical glass preform (11), which extends along an axial direction (X) and has at least one open end (6). This glass preform (11) features a shaped section (13) that extends from the open end (6) in an axial direction (X) and is in a formable state.

The formable state is normally achieved by means of heating the glass, in which context the temperature is in a range between 1000° C. and 1200° C., preferably approximately 1100° C. The hollow, cylindrical glass preform (11) is arranged in a holding device (26) such that said preform is rotatable, whereby the axis of rotation is an axial centre line (27) of the hollow, cylindrical glass preform (11). Consistent shaping of the glass preform is ensured by a rotation thereof.

Furthermore, FIGS. 1 and 2 show a second shaping tool (14), by means of which at least the shaped section (13) of the hollow, cylindrical glass preform (11) is shaped. The shaped section (13) is shaped by means of the second shaping tool (14) such that an inner surface (10) of the shaped section (13) fits against a shaping pin (16), as a result of which the shaped section (13) forms a channel (5). The second shaping tool (14) comprises two shaping rollers (14a, 14b) which are spaced apart from one another. In the configuration shown in FIG. 1, the shaping rollers (14a, 14b) are located in a first position, in which they are spaced apart by a first distance (22). If the shaping rollers (14a, 14b) are located in this first position, at least the shaped section (13) of the hollow, cylindrical glass preform (11) is displaced between the shaping rollers (14a, 14b). This can take place by means of, for example, an appropriate transport device, which feeds the glass preforms to the device and transports them to the next production step after processing.

Furthermore, FIGS. 1 and 2 show a third shaping tool (15), which features a shaping pin (16). This shaping pin (16) preferably consists of a non-metallic material, preferably a technical ceramic or a ceramic-like material, and particularly preferably consists of silicon nitrate ($Si_3N_4$) or glass-like carbon. The shaping pin (16) is secured using a securing means (28) of the third shaping tool (15) and displaced along the axial direction (X), through the open end (12) of the hollow, cylindrical glass preform (11), and into the shaped section (13) of said preform.

In the configuration shown in FIG. 2, the shaping rollers (14a, 14b) are located in a second position. In this second position, the shaping rollers (14a, 14b) are spaced apart from one another by a second distance (24). This second distance (24) is smaller than the first distance (22). The shaping rollers lie against the shaped section (13) of the glass preform (11), as a result of which a deforming force is applied to the shaped section (13). As a consequence, an external shaping of the shaped section (13) is accomplished. The internal shaping of the shaped section (13) or the shaping of the channel (5) is accomplished by means of restraining the shaping pin (16). The shape of the channel (5) in this case depends on the shape of the shaping pin (16). In order to increase the service life of the shaping pin, it is advantageous for the shaping pin to be cooled by a cooling means.

Figure 4:
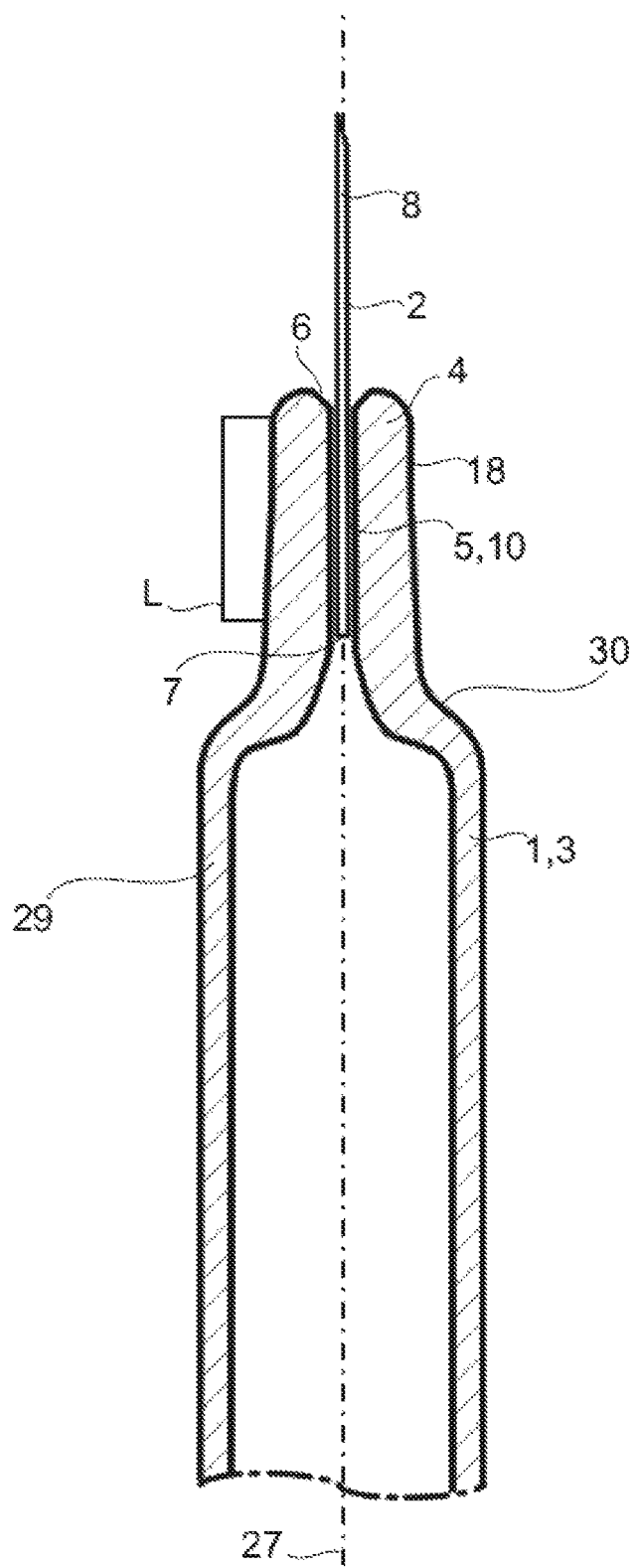
FIG. 4 shows a sectional view of a syringe body having a piercing means.

A syringe body (3) produced in this manner is shown in FIG. 3. FIG. 4 shows a syringe body having a piercing means (2) secured therein. The syringe body is designed as a hollow cylinder and features a main section (29), inside the chamber of which the medium being administered is kept. The outer diameter of the main section (29) is larger than the outer diameter of the distal end section (4), with a transitional area (30) being located between the main section (29) and the distal end section. The inner diameter of the distal end section (4) is likewise smaller than the inner diameter of the main section (29). The inner channel (5) of the distal end section (4) is in this case connected to the chamber of the main section (29).

Moreover, the distal end section (4) is normally conical in shape. Syringe bodies of this kind are frequently equipped with a finger flange at the proximal end thereof (not shown in the drawings). Furthermore, after the syringe is filled with the appropriate medium, a plunger having a stopper is inserted into the proximal opening of the syringe body (3) (likewise not shown in the drawings).

Figure 3A:
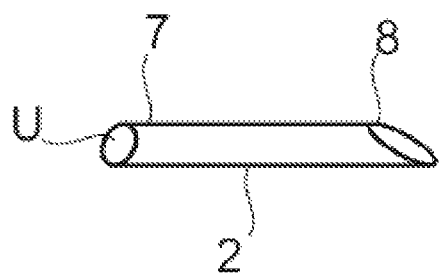
FIG. 3a shows a view of a piercing means.

FIG. 3a shows a piercing means (2). The piercing means is designed as a hollow cylinder and features a proximal section (7) as well as a distal section (8). An appropriate cutis applied to the distal section (8). The piercing means furthermore features a circumference (U).

The method for producing a syringe (1) having a piercing means (2) is shown in FIGS. 5 to 8 and comprises the following steps:
a) providing a syringe body (3) having a distal end section (4), which comprises an inner channel (5) that discharges at a distal opening (6), whereby the distal end section (4) is in a formable state;
b) providing a piercing means (2);
c) inserting a proximal section (7) of the piercing means (2) through the distal opening (6) into the inner channel (5) of the distal end section (4);
d) shaping the distal end section (4) by means of a first shaping tool (9) in such a way that an inner surface (10) of the distal end section (4) contacts at least portions of the piercing means (2), as a result of which at least portions of the piercing means (2) are secured.

The first shaping tool (9) comprises two shaping rollers (9a, 9b) spaced apart from one another, whereby, in a first position, the shaping rollers (9a, 9b) are spaced apart by a first distance (21), whereby the distal end section (4) is displaceable between the shaping rollers (9a, 9b) when the shaping rollers (9a, 9b) are located in the first position.

After the syringe body (3) has been shaped from the hollow, cylindrical glass preform (11) and after the removal of the shaping pin (16) from the channel (5), the syringe body (3) is removed from the gap between the shaping rollers (14a, 14b) of the second shaping tool (14) and placed in a gap between the shaping rollers (9a, 9b) of the first shaping tool (9).

The shaping of the distal end section (4) in step d) can take place immediately after the syringe body (3) is produced. Alternatively, if the distal end section is no longer in a formable state, the syringe body (3) can initially be subjected to an additional process, in which the distal end section (4) is heated so that it is again transformed into a formable state.

Using a holding means (17), the piercing means (2) is initially inserted along the axial centre line (27) of the syringe body (3) into the channel (5) of the distal end section (4). After the piercing means (2) has been inserted into the channel (5), the shaping rollers (9a, 9b) are displaced into a second position, in which they are spaced apart by a second distance (23), which is smaller than the first distance (21). In this position, a deforming force is applied to the distal end section (4) by means of the shaping rollers (9a, 9b), as a result of which a shaping of the distal end section (4) is able to be accomplished, and the inner surface of the distal end section (4) is pressed against the piercing means (2).

In steps b) and c) in particular, the piercing means (2) is in this case rotatably mounted in a holding means (17). By means of said rotatable mounting, the orientation of the piercing means (2), in particular the cut of the piercing means (2), can be oriented in relation to the syringe body.

The hollow, cylindrical glass preform is arranged in the holding device (26) such that said preform is rotatable, whereby the axis of rotation is the axial centre line of the hollow, cylindrical glass preform or of the syringe body. The third shaping tool, which has the shaping pin, is preferably arranged centrically with respect to said axial centre line.

By means of the inner surface (10) being pressed against the piercing means (2), the shaping rollers (9a, 9b) remain in a fixed position. In order to then achieve contact for the piercing means around the entire circumference (U) of the piercing means (2), the syringe body (3) is rotated accordingly by means of the holding device (26). During this process, the piercing means (2) can then be rotated by means of the rotatable holding device (17) in a manner appropriately synchronous with the holding device (26) for the syringe body (3). As an alternative, after having initially been secured in places, the piercing means (2) can be released from its holder enough to allow rotation of the syringe body. Due to having initially been secured in places, a sufficiently strong frictional connection already exists in order to ensure doing so. As a result, the holder (17) then functions only as a guide for rotating the piercing means (2).

It would also be conceivable for both the shaping of the shaped section (13) of the hollow, cylindrical glass preform (11) and the further shaping of the distal end section (4) to take place by means of the same first shaping tool (9). For this purpose, after the distal end section (4) has been shaped from the shaped section (13) of the hollow, cylindrical glass preform (11), the shaping pin (16) is removed from the channel (5) before removing the third shaping tool (15) from the shaping rollers (9a, 9b). Subsequently, by means of the holding device (17), the piercing means (2) is inserted centrically along the axial centre line (27) of the syringe body (3).

The distal end section (4) has a length (L). According to an embodiment, the shaping in step d) takes place along at least a sub-section (18) of the length (L). A contact section (19) of the channel or rather the inner surface (10) of the distal end section (4) contacts the piercing means (2) thereby. The length (L) of the distal end section (4) extends between a main section (29) of the syringe body (3), in the chamber of which the medium can be kept—or rather the transitional area (30) between the main section (29) and the distal end section (4)—and the distal opening (6), through which the piercing means (2) was inserted.

The contact section (19) of the channel (5) originates in the transitional area (30) and extends along a sub-section (18) of the length (L). The contact in the contact section (19) takes place around the entire circumference (U) of the piercing means (2). The entire circumference (U) of the piercing means (2) is thus entirely enclosed by the contact section. As a result, the piercing means (2) is secured in at least a rudimentary manner and, in addition, the channel (5) closes completely around the piercing means (2). As a consequence, contamination is unable to enter through the channel (5) into the chamber of the main section (29) of the syringe body (3).

It is advantageous for the contact section (19) to extend along 5% to 90% of the length (L) of the distal end section (4), preferably along 20% to 80% of the length (L) of the distal end section (4), and particularly preferably along 30% to 50% of the length (L) of the distal end section (4).

Figure 5:
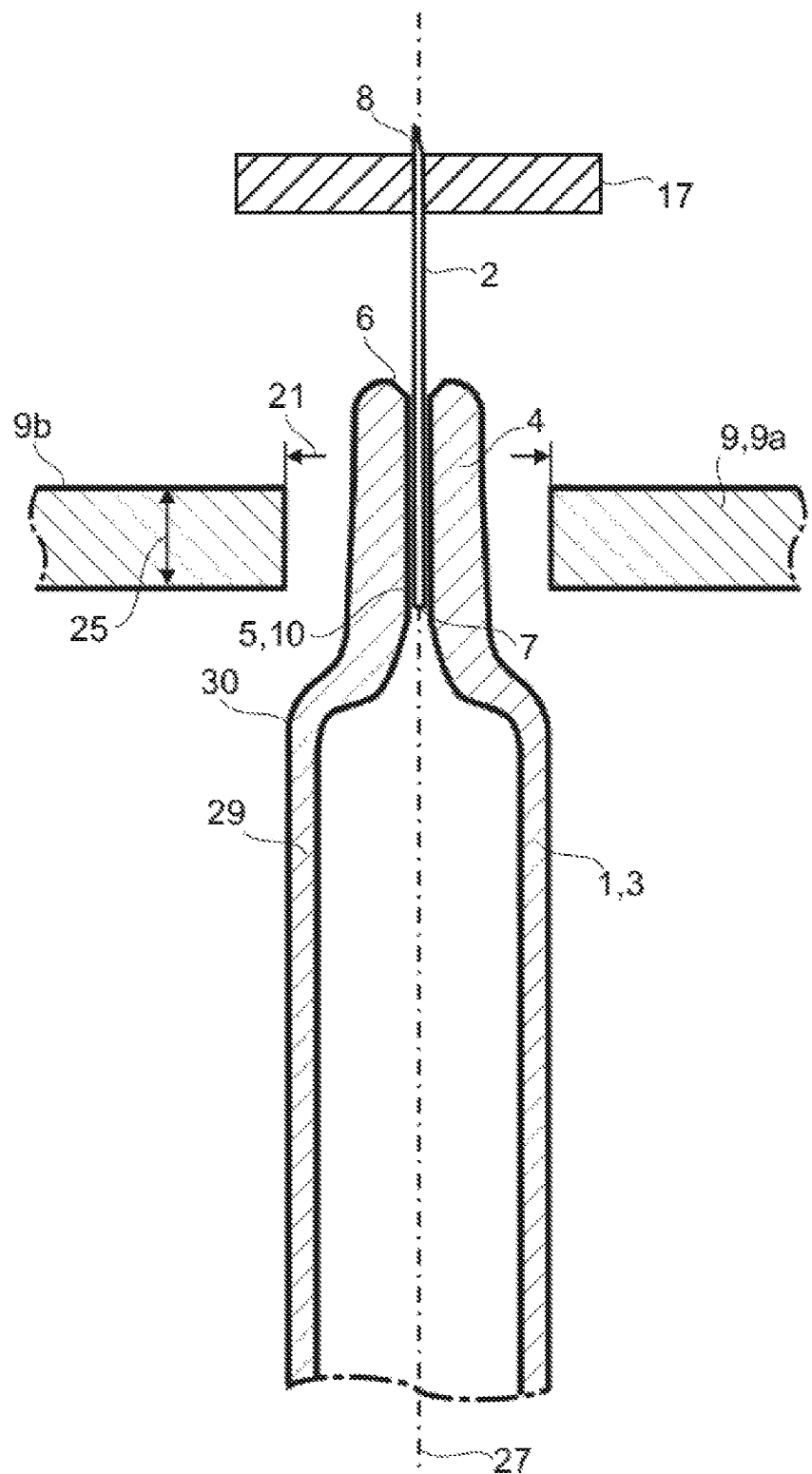
FIG. 5 is a schematic depiction of a method for producing a syringe body having a piercing means in an embodiment of the invention.
Figure 6:
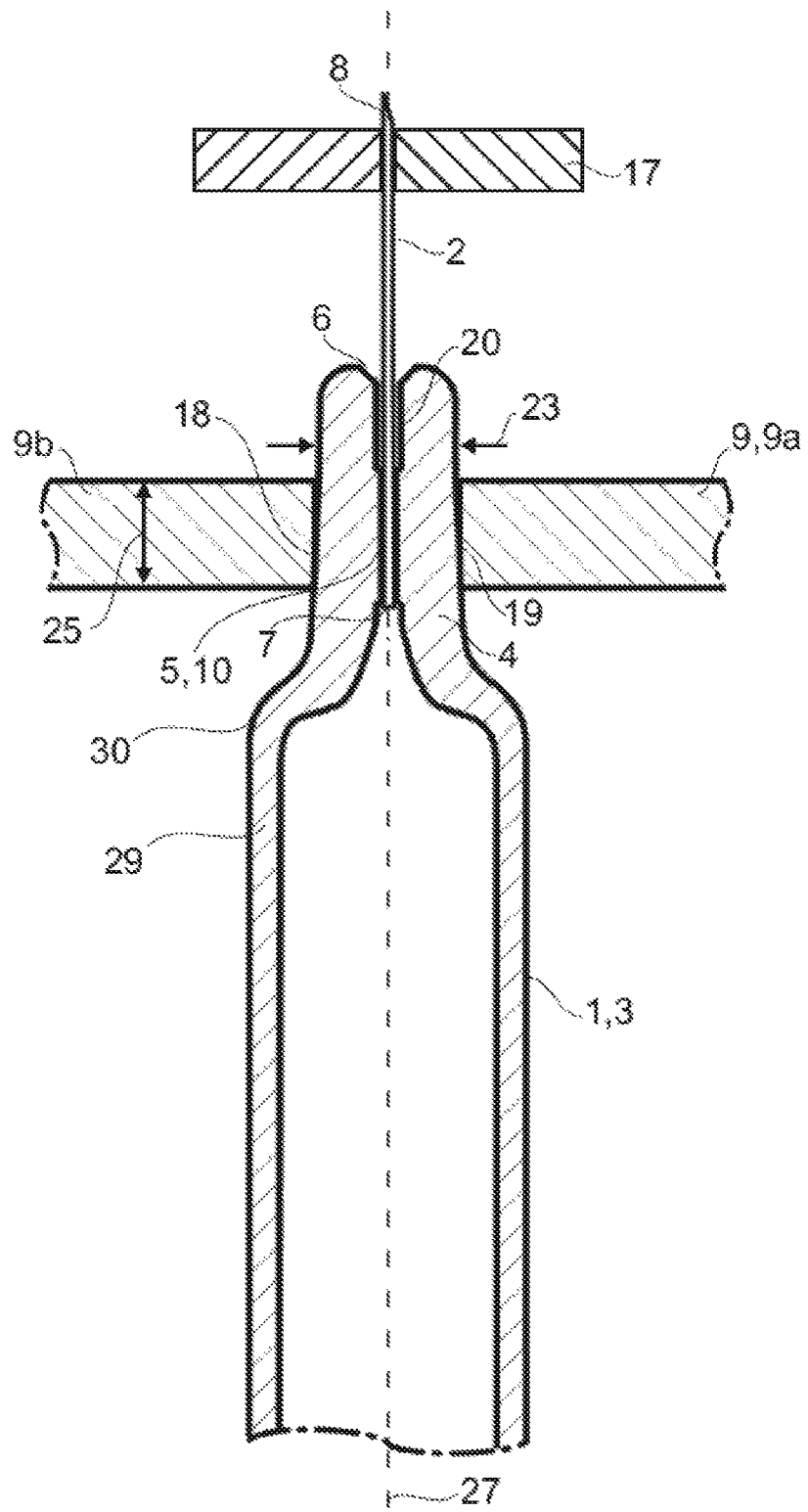
FIG. 6 is a further schematic depiction of the method for producing a syringe body having a piercing means.

The shaping rollers (9a, 9b) of the first shaping tool (9) clearly need to have a width (25) which is smaller than the length (L) of the distal end section (4) or, rather, the length of the contact section (19). This is shown in FIGS. 5 and 6. In the event that both the shaping of the shaped section (13) of the hollow, cylindrical glass preform (11) and the further shaping of the distal end section (4) takes place by means of the same first shaping tool (9), the shaping rollers (9a, 9b) need to have an adjustable width.

The distal section (20) of the channel (5) extends between the contact section (19) of the channel (5) and the distal opening (6). Within this area, the inner surface (10) of the distal end section (4) does not lie against the piercing means (2)

Following the shaping in step d), a preferably organic adhesive is introduced into the distal section (20) through the distal opening (6), thereby further securing the piercing means (2) in the channel (5). By means of this adhesion, a pullout force of at least 30N, preferably at least 60N, and more preferably at least 90N is achieved. The term pullout force is understood as meaning a force necessary in order to pull the piercing means (2) out of the distal end section (4). The use of a polymer-based or epoxy-based adhesive is preferable.

According to a further embodiment, the shaping in step d) takes place across essentially the entire length (L) of the distal end section (4). The contact section (19) of the channel (5) or rather the inner surface (10) of the distal end section (4) then contacts the piercing means (2) across essentially the entire length (L) of the distal end section (4). The contact section (19) of the channel (5) originates in the transitional area (30) and extends along essentially the entire length (L).

The contact in the contact section (19) takes place around the entire circumference (U) of the piercing means (2). The entire circumference (U) of the piercing means (2) is thus enclosed by the contact section. As a result, the piercing means (2) is secured and, in addition, the channel (5) closes completely around the piercing means (2). As a consequence, contamination is unable to enter through the channel (5) into the chamber of the main section (29) of the syringe body (3). As a result of the greater contact surface between the piercing means (2) and the contact section (19), a pullout force of at least 30N can be achieved without the use of an additional adhesive.

Figure 7:
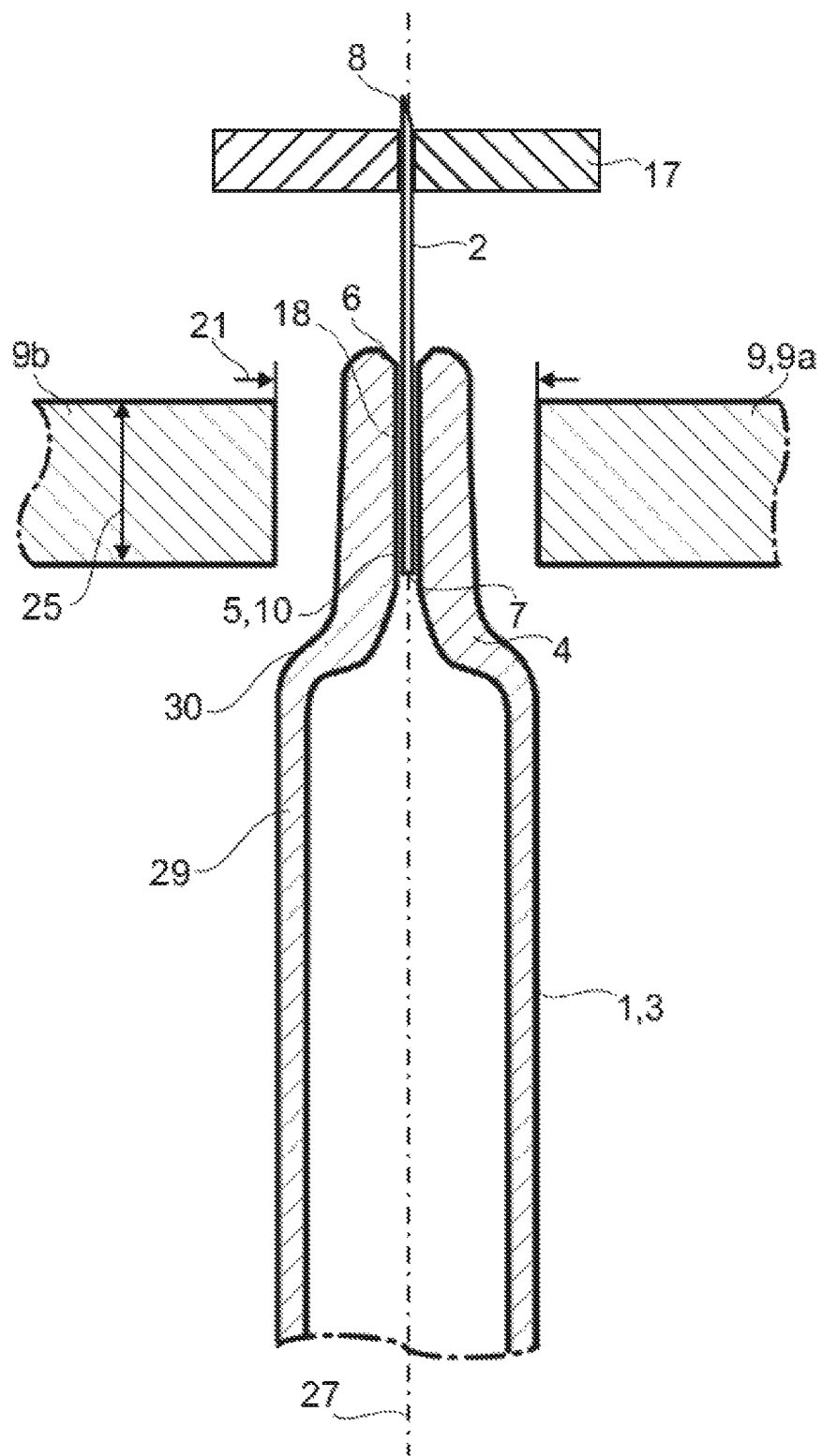
FIG. 7 is a schematic depiction of a further method for producing a syringe body having a piercing means.
Figure 8:
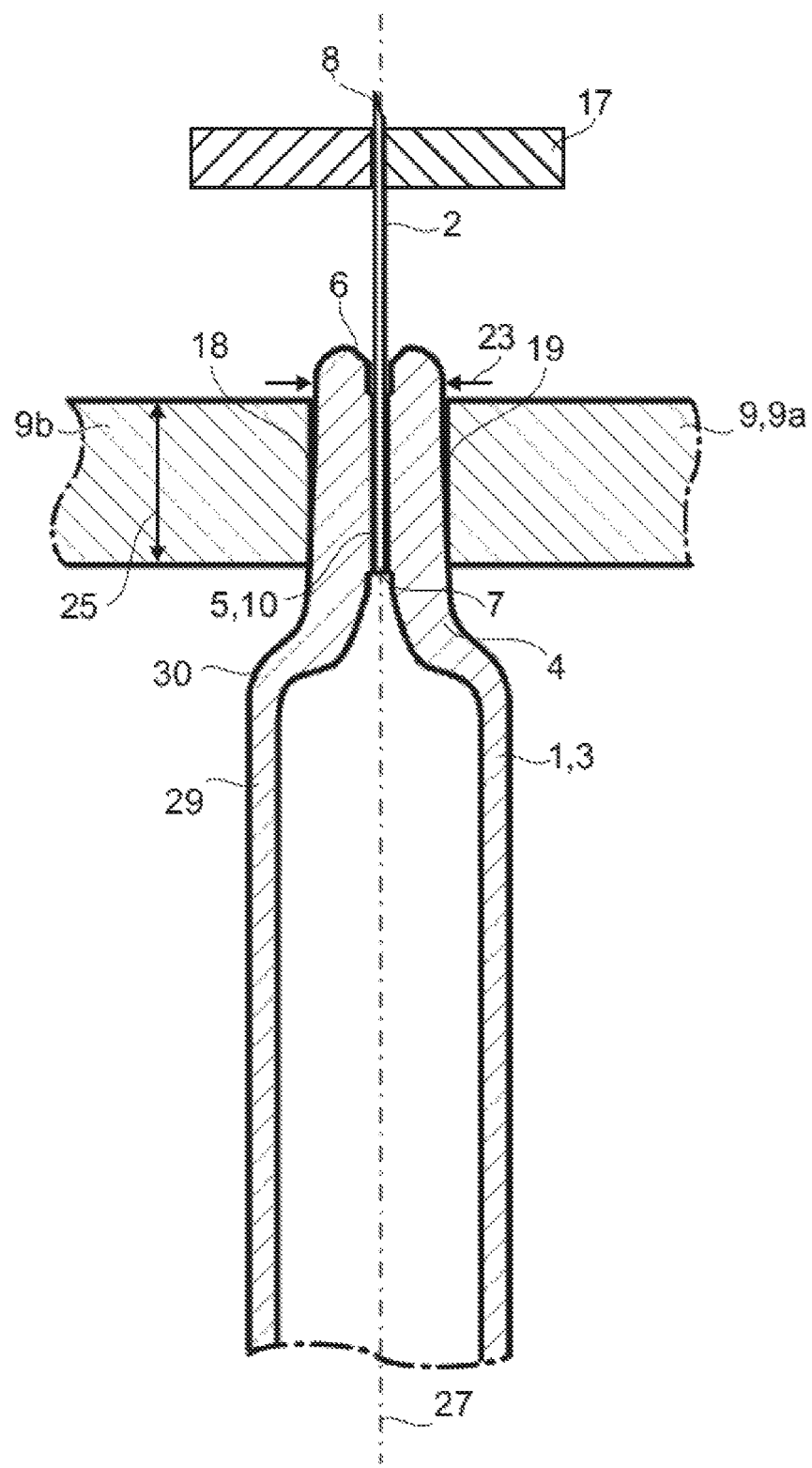
FIG. 8 is a further schematic depiction of a further method for producing a syringe body having a piercing means.

The shaping rollers (9a, 9b) of the first shaping tool (9) clearly then need to have a width (25) which is essentially the same as the length (L) of the distal end section (4). This is shown in FIGS. 7 and 8.

All of the features disclosed in the application documents are claimed as being essential to the invention insofar as they are novel with respect to the prior art either individually or in combination.

Having now fully described the present invention in some detail by way of illustration and examples for purposes of clarity of understanding, it will be obvious to one of ordinary skill in the art that the same can be performed by modifying or changing the invention within a wide and equivalent range of conditions, formulations and other parameters without affecting the scope of the invention or any specific embodiment thereof, and that such modifications or changes are intended to be encompassed within the scope of the appended claims.

When a group of materials, compositions, components or compounds is disclosed herein, it is understood that all individual members of those groups and all subgroups thereof are disclosed separately. Every formulation or combination of components described or exemplified herein can be used to practice the invention, unless otherwise stated. Whenever a range is given in the specification, for example, a temperature range, a time range, or a composition range, all intermediate ranges and subranges, as well as all individual values included in the ranges given are intended to be included in the disclosure. Additionally, the end points in a given range are to be included within the range. In the disclosure and the claims, "and/or" means additionally or alternatively. Moreover, any use of a term in the singular also encompasses plural forms.

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. Any recitation herein of the term "comprising", particularly in a description of components of a composition or in a description of elements of a device, is understood to encompass those compositions and methods consisting essentially of and consisting of the recited components or elements.

One of ordinary skill in the art will appreciate that starting materials, device elements, analytical methods, mixtures and combinations of components other than those specifically exemplified can be employed in the practice of the invention without resort to undue experimentation. All art-known functional equivalents, of any such materials and methods are intended to be included in this invention. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. The invention illustratively described herein suitably may be practiced in the absence of any element or elements, limitation or limitations which is not specifically disclosed herein. Headings are used herein for convenience only.

All publications referred to herein are incorporated herein to the extent not inconsistent herewith. Some references provided herein are incorporated by reference to provide details of additional uses of the invention. All patents and publications mentioned in the specification are indicative of the levels of skill of those skilled in the art to which the invention pertains. References cited herein are incorporated by reference herein in their entirety to indicate the state of the art as of their filing date and it is intended that this information can be employed herein, if needed, to exclude specific embodiments that are in the prior art.

LIST OF REFERENCE SIGNS

1 Syringe
2 Piercing means
3 Syringe body
4 Distal end section of the syringe body
5 Channel
6 Distal opening, open distal end
7 Proximal section of the piercing means
8 Distal section of the piercing means
9 First shaping tool
9a, 9b Shaping rollers of the first shaping tool
10 Inner surface of the distal end section
11 Hollow, cylindrical glass preform
12 Open distal end of the hollow, cylindrical glass preform
13 Shaped section
14 Second shaping tool
14a, 14b Shaping rollers of the second shaping tool
15 Third shaping tool
16 Shaping pin
17 Holding device
18 Sub-section of the length (L)
19 Contact section of the channel
20 Distal section of the channel
21 First distance between the shaping rollers of the first shaping tool
22 First distance between the shaping rollers of the second forming tool 23 Second distance between the shaping rollers of the first shaping tool
24 Second distance between the shaping rollers of the second forming tool
25 Width of the shaping rollers of the first shaping tool
26 Holding device for the hollow, cylindrical glass preform
27 Axial centre line of the hollow, cylindrical glass preform or the syringe body
28 Securing means of the third shaping tool
29 Main section of the syringe body
30 Transitional area
L Length of the distal end section
X Axial direction
U Circumference of the piercing means

We claim:

1. A method for producing a syringe having a piercing means, comprising the following steps:
   a) providing a syringe body having a distal end section, which comprises an inner channel that discharges at a distal opening, wherein the distal end section is in a formable state;
   b) providing a piercing means;
   c) while the distal end section is in the formable state, inserting a proximal section of the piercing means through the distal opening into the inner channel of the distal end section; and
   d) shaping the distal end section by means of a first shaping tool in such a way that an inner surface of the distal end section contacts at least portions of the piercing means, as a result of which at least portions of the piercing means are secured,
   wherein in steps b) and c), the piercing means is rotatably mounted in a holding device.

2. The method according to claim 1, wherein producing the syringe body comprises the following steps:
   aa) providing a hollow, cylindrical glass preform, which extends along an axial direction (X) and has at least one open distal end, wherein the glass preform features a shaped section that extends from the at least one open distal end in a radial direction (X) and is in a formable state; and
   bb) shaping the shaped section to a cone-shaped distal end section of the syringe body by means of a second and a third shaping tool.

3. The method according to claim 2, wherein an initial shaping of the distal end section in step bb) and a further shaping of the distal end section in step d) takes place by means of the first shaping tool.

4. The method according to claim 2, wherein step bb) comprises the following sub-steps:
   (1) providing the second shaping tool, by means of which at least the shaped section of the hollow, cylindrical glass preform is able to be shaped;
   (2) providing a third shaping tool, which features a shaping pin;
   (3) inserting the shaping pin through the at least one open distal end of the hollow, cylindrical glass preform and into the shaped section thereof;
   (4) shaping the shaped section by means of the second shaping tool such that the inner surface of the shaped section fits against the shaping pin, as a result of which the shaped section forms a channel; and
   (5) removing the shaping pin from the channel.

5. The method according to claim 4, wherein the shaping pin consists of a non-metallic material.

6. The method according to claim 5, wherein the non-metallic material is a technical ceramic, a ceramic-like material, or glass-like carbon.

7. The method according to claim 4, wherein the first shaping tool comprises two first shaping rollers spaced apart from one another, wherein, in a first position of the first shaping rollers, the first shaping rollers are spaced apart by a first distance of the first shaping rollers, and wherein the distal end section is displaceable between the first shaping rollers when the first shaping rollers are located in the first position of the first shaping rollers,
   wherein a second shaping tool comprises two second shaping rollers spaced apart from one another, wherein, in a first position of the second shaping rollers, the second shaping rollers are spaced apart by a first distance of the second shaping rollers, and wherein the distal end section is displaceable between the second shaping rollers when the second shaping rollers are located in the first position of the second shaping rollers.

8. The method according to claim 7, wherein the second shaping rollers of the second shaping tool are displaceable into a second position of the second shaping rollers, in which they are spaced apart by a second distance of the second shaping rollers, which is smaller than the first distance of the second shaping rollers, wherein, in the second position of the second shaping rollers, a deforming force is able to be applied to the shaped section of the hollow, cylindrical glass preform by means of the second shaping rollers, as a result of which the external shaping of the shaped section can be accomplished, and wherein an internal shaping of the shaped section can be accomplished by means of the shaping pin of the third shaping tool.

9. The method according to claim 7, wherein the first shaping rollers of the first shaping tool have a width, which is smaller than or equal to the length (L) of the distal end section, and they are displaceable into a second position of the first shaping rollers, in which they are spaced apart by a second distance of the first shaping rollers, which is smaller than the first distance of the first shaping rollers, wherein, in the second position of the first shaping rollers, a deforming force is able to be applied to the distal end section by means of the first shaping rollers, as a result of which a shaping of the distal end section is able to be accomplished, and the inner surface of the distal end section is pressed against the piercing means.

10. The method according to claim 1, wherein the distal end section has a length (L), wherein the shaping in step d) takes place along a sub-section of the length (L), as a result of which a contact section of the inner channel or the inner surface of the distal end section contacts the piercing means as a result of which, the piercing means is secured, thereby achieving complete contact around the circumference (U) of the piercing means with the inner surface of the distal end section.

11. The method according to claim 10, wherein following the shaping in step d), an adhesive is introduced through the distal opening into a distal section of the inner channel, thereby securing the piercing means in the distal end section such that a pullout force of at least 30N is achieved without use of an additional adhesive, wherein the distal section of the inner channel is limited by the distal opening and the contact section of the inner channel.

12. The method according to claim 11, wherein the adhesive is an organic adhesive.

13. The method according to claim 1, wherein the shaping of the distal end section in step d) takes place immediately after the syringe body is produced, or the syringe body is initially subjected to an additional process, in which the distal end section is heated so that it is again transformed into a formable state.

14. The method according claim 1, wherein the shaping in step d) takes place across essentially an entire length (L) of the distal end section, as a result of which a contact section of the inner channel or the inner surface of the distal end section contacts and secures the piercing means such that a pullout force of at least 30N is achieved without use of an additional adhesive, thereby achieving complete contact around the circumference (U) of the piercing means with the inner surface of the distal end section.

15. The method according to claim 1, wherein following step d), having been provided with the piercing means, the syringe body is cooled and/or subjected to a sterilisation process.

16. A method for producing a syringe having a piercing means, comprising the following steps:
   a) providing a syringe body having a distal end section, which comprises an inner channel that discharges at a distal opening, wherein the distal end section is in a formable state;
   b) providing a piercing means;
   c) while the distal end section is in the formable state, inserting a proximal section of the piercing means through the distal opening into the inner channel of the distal end section;
   d) shaping the distal end section by means of a first shaping tool in such a way that an inner surface of the distal end section contacts at least portions of the piercing means, as a result of which at least portions of the piercing means are secured,
   wherein the distal end section has a length (L), wherein the shaping in step d) takes place along a sub-section of the length (L), as a result of which a contact section of the inner channel or the inner surface of the distal end section contacts the piercing means as a result of which, the piercing means is secured, thereby achieving complete contact around the circumference (U) of the piercing means with the inner surface of the distal end section,
   wherein following the shaping in step d), an adhesive is introduced through the distal opening into a distal section of the inner channel, thereby securing the piercing means in the distal end section such that a pullout force of at least 30N is achieved without use of an additional adhesive, wherein the distal section of the channel is limited by the distal opening and the contact section of the channel.

17. The method according to claim 16, wherein producing the syringe body comprises the following steps:
   aa) providing a hollow, cylindrical glass preform, which extends along an axial direction (X) and has at least one open distal end, wherein the glass preform features a shaped section that extends from the at least one open distal end in a radial direction (X) and is in a formable state;
   bb) shaping the shaped section to a cone-shaped distal end section of the syringe body by means of a second and a third shaping tool.

18. The method according to claim 17, wherein step bb) comprises the following sub-steps:
   (1) providing the second shaping tool, by means of which at least the shaped section of the hollow, cylindrical glass preform is able to be shaped;
   (2) providing a third shaping tool, which features a shaping pin;
   (3) inserting the shaping pin through the at least one open distal end of the hollow, cylindrical glass preform and into the shaped section there-of;
   (4) shaping the shaped section by means of the second shaping tool such that the inner surface of the shaped section fits against the shaping pin, as a result of which the shaped section forms a channel;
   (5) removing the shaping pin from the channel.

19. A method for producing a syringe having a piercing means, comprising the following steps:
   a) providing a syringe body having a distal end section, which comprises an inner channel that discharges at a distal opening, wherein the distal end section is in a formable state;
   b) providing a piercing means;
   c) while the distal end section is in the formable state, inserting a proximal section of the piercing means through the distal opening into the inner channel of the distal end section;
   d) shaping the distal end section by means of a first shaping tool in such a way that an inner surface of the distal end section contacts at least portions of the piercing means, as a result of which at least portions of the piercing means are secured,
   wherein producing the syringe body comprises the following steps:
   aa) providing a hollow, cylindrical glass preform, which extends along an axial direction (X) and has at least one open distal end, wherein the glass preform features a shaped section that extends from the at least one open distal end in a radial direction (X) and is in a formable state;
   bb) shaping the shaped section to a cone-shaped distal end section of the syringe body by means of a second and a third shaping tool,
   wherein an initial shaping of the distal end section in step bb) and a further shaping of the distal end section in step d) takes place by means of the first shaping tool.

20. The method according to claim 19, wherein step bb) comprises the following sub-steps:
   (1) providing the second shaping tool, by means of which at least the shaped section of the hollow, cylindrical glass preform is able to be shaped;
   (2) providing a third shaping tool, which features a shaping pin;
   (3) inserting the shaping pin through the at least one open distal end of the hollow, cylindrical glass preform and into the shaped section thereof;
   (4) shaping the shaped section by means of the second shaping tool such that the inner surface of the shaped section fits against the shaping pin, as a result of which the shaped section forms a channel;
   (5) removing the shaping pin from the channel.

* * * * *